United States Patent [19]

Amin

[11] 4,317,238
[45] Mar. 2, 1982

[54] ADJUSTABLE CAP KIT

[76] Inventor: Armando Amin, 1320 NW. 3 St., Apt. 4, Miami, Fla. 33125

[21] Appl. No.: 139,409

[22] Filed: Apr. 11, 1980

[51] Int. Cl.³ .............................. A42B 1/20; A42B 1/22
[52] U.S. Cl. ................................................ 2/12; 2/197; 2/DIG. 11
[58] Field of Search ............... 2/12, 171, 195, 197, 2/200, 196, DIG. 11; 24/17 A, 222, 201 A, 201 HE, 230 R, 265 R, 265 H

[56] References Cited

U.S. PATENT DOCUMENTS

| 216,543 | 6/1879 | Weaver | 24/17 A |
|---|---|---|---|
| 1,333,102 | 3/1920 | Dietsche | 24/17 A |
| 1,631,210 | 6/1927 | Johnson | 2/12 |
| 2,004,098 | 6/1935 | Andrews | 2/197 X |
| 2,521,017 | 9/1950 | Moen et al. | 2/DIG. 11 |
| 2,679,711 | 6/1954 | Learnard | 2/197 X |
| 2,701,367 | 2/1955 | Berg | 2/200 X |
| 2,988,743 | 6/1961 | Wagenfeld | 2/12 |

Primary Examiner—Peter P. Nerbun
Attorney, Agent, or Firm—John Cyril Malloy

[57] ABSTRACT

An adjustable cap kit including a first band member having first and second ends with male connection means and a bottom lateral edge with slit means adjacent thereto, a second band member having first and second ends with female connectors for compatible locking engagement with the first band member, a reinforcing member with first and second ends and a plurality of generally rectangular openings spaced apart throughout the length of the reinforcing member and a brim member having a visor portion and an inner abutment edge, the inner abutment edge including a plurality of spaced apart male connection means for compatible interengagement with the first band member slits and the reinforcing member openings.

9 Claims, 13 Drawing Figures

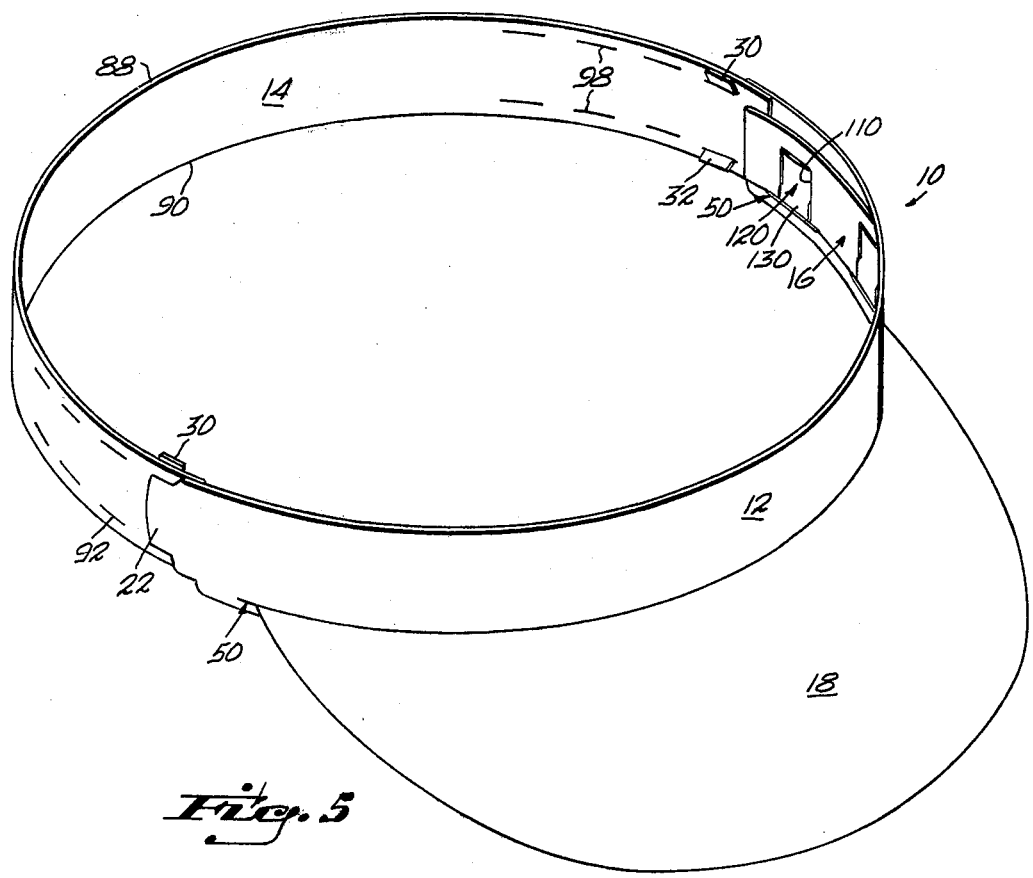
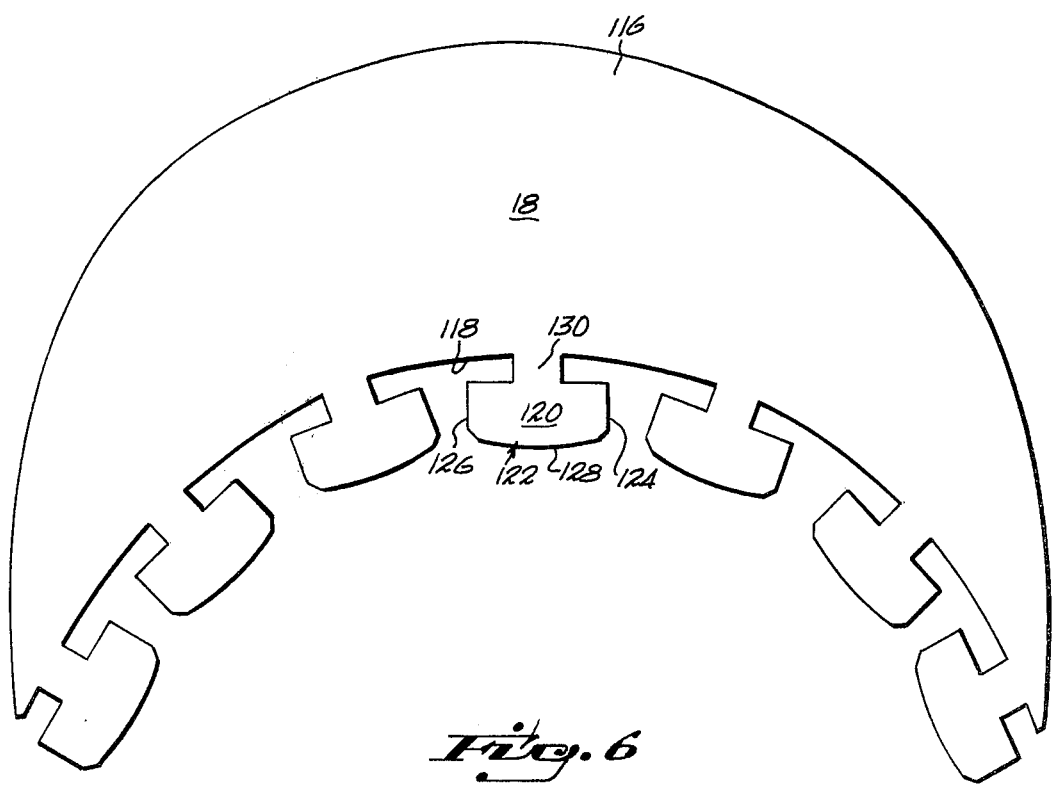

ADJUSTABLE CAP KIT

BACKGROUND OF THE INVENTION

1. Technical Field

This invention generally relates to kits and, more particularly, to adjustable cap kits.

A number of chain restaurants such as McDonalds and Burger King have found it useful in the commercialization of their product to use hats bearing their distinctive logos for their store personnel.

In all likelihood, a chain operation wants their hat to reflect well upon the institution itself. The applicant having studied the situation and found the caps currently available to chain operations not acceptable has developed a device in kit form which it is believed will reflect well upon the institution and prove to be cost effective in the long run.

Applicant's kit is readily adjustable and capable of easy assembly by even the most unsophisticated of the chain personnel. Further, once assembled, applicant's kit is of an unusual durability provided by its well conceived design.

The applicant's kit may also be used for promotional use as is currently used in chain restaurants. In this way, the applicant's kit will reflect well upon the institution promoting since the hat is durable and well designed. Further, even the most unsophisticated child or adult will find the assembly of the kit quite simple.

Further, the hat employs patterns which could be made of sheets of plastic such that the sheet itself would be used to its maximum efficiency.

In general, the assembled cap is attractive but durable and reflects well upon the institution employing it.

2. Summary of the Invention

An adjustable cap kit comprising a first band member of predetermined length having first and second end zones comprising male connection means. Upper lower lateral edges spanning the first and second connection means. Slit means adjacent the lower edge.

A second band member also of a predetermined length generally equal to the predetermined length of the first band member having first and second ends and upper and lower edges spanning the ends. The second band member includes slit mean pairs generally along the length of the second band member.

A reinforcing member of a predetermined length somewhat smaller than the predetermined length of the band members and having a plurality of spaced apart openings along its length.

A brim member having a visor portion with an inside edge defining an abutment edge and including male connection means spaced apart along the abutment edge. The male connection means is sized and shaped for compatible interengagement with the first band member slits and reinforcing member openings.

In accordance with these and other objects which will become apparent hereinafter, the instant invention will now be described with reference to the accompanying drawings in which:

DESCRIPTION OF THE DRAWINGS

FIG. 5 is a view of the invention in assembled form;

FIG. 6 is an elevational view of the brim member;

DESCRIPTION OF THE PREFERRED EMBODIMENT

Figure 2:
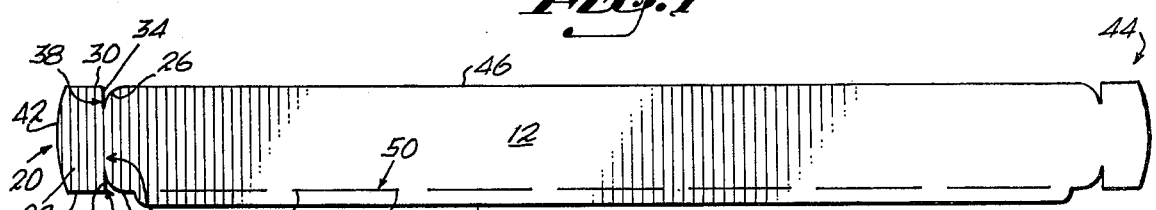
FIG. 2 is an elevational view of the first band member showing a particular embodiment of the male connection means.

Referring to the drawings wherein like reference characters designate like or corresponding parts throughout the several views and referring particularly to FIG. 5, there is shown the invention an adjustable hat kit generally denoted by the numeral 10. The hat kit includes a first front band member 12, a second rear band member 14, a reinforcing member 16, and a brim member 18. With particular reference to FIG. 2 there is shown the first band member 12 being of a predetermined length and including a first male connection means generally denoted by the numeral 20. The first male connection means 20 includes a head portion 22 connected to the band member 12 via neck zone 24 comprising a pair of arcuate shaped top and bottom edges 26 and 28 respectively. The head comprises top and bottom horizontal edge portions 30 and 32 respectively with inwardly extending side edges 34 and 36 connecting at the neck zone 24 thereby defining top and bottom shoulders 38 and 40 respectively. The head includes a terminal edge spanning the top and bottom horizontal side edge generally denoted by the numeral 42 and is generally of an arcuate shape although as will be readily appreciated by one skilled in the art, the terminal edge may also be generally horizontal. The first band member includes a second end zone 44 which is identical to the first male connection means.

The first band member 12 includes top and bottom lateral edges 46 and 48 extending between the first and second male connection means generally horizontal and generally straight. Spaced a predetermined distance from the lower horizontal edge 48 are slit means such as at 50 having terminal ends 52 and 54 spaced a predetermined distance from each other and extending generally from the first male connection means to the second male connection means.

It will readily be appreciated that other male connection means may be used within the scope of this invention. Applicant has further developed and refined an alternative male connection means which may be used in place of one or both of the male connection means described above.

Figure 12:
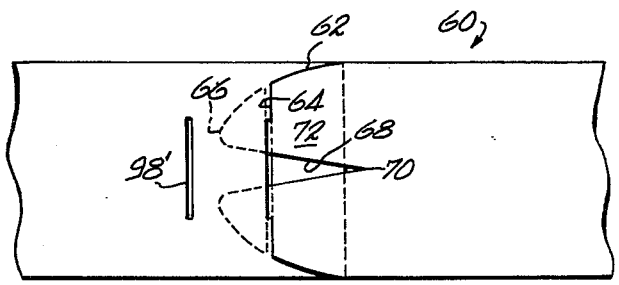
FIG. 12 is a partial fragmentary view of an alternative embodiment of male and female connection means for the band members in hooked-up engagement.
Figure 13:
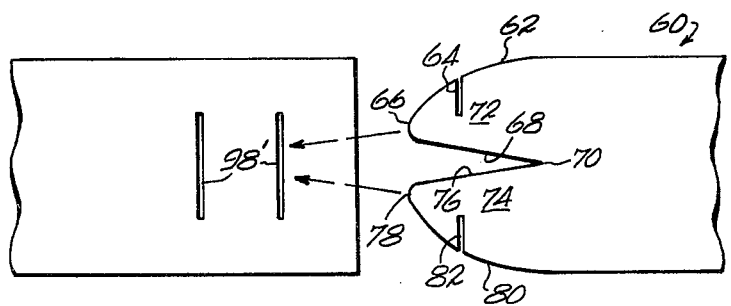
FIG. 13 is an unconnected view of the embodiment shown in FIG. 12.

In the alternative embodiment pictured in FIGS. 12 and 13, the male connection means generally denoted by the numeral 60 includes a head portion having an arcuate outer edge 62 with a vertical notch 64 and a terminal end 66, the notch 64 being spaced a predetermined distance from the terminal end 66. An inner edge 68 extends angularly and inwardly from the terminal end and terminates essentially within the means 60 at a point such as 70 thereby defining a top tab member generally denoted by the numeral 72.

A bottom tab member 74, identical in all respects to the top tab member with the exception that the elements are in the reverse order begins at point 70 with an angular inwardly extending straight edge such as at 76 having a terminal end 78 in a common vertical plane as terminal end 76 with an outer edge 80 arcuately shaped and having a vertical notch 82 in a common vertical plane as 64 thereby defining an alternative male connection means comprising a V-shaped head.

Figure 3:
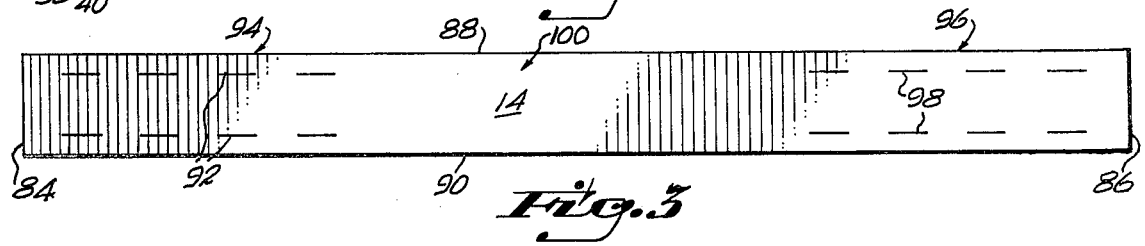
FIG. 3 is an elevational view of the second band member showing a particular embodiment of the slit means.

With particular reference to FIG. 3 there is shown the rear band member 14 of a predetermined length and including a first end 84 and a second end 86. Spanning the ends are upper and lower lateral horizontal edges 88 and 90. The rear band 14 may be divided in three sections. The first section adjacent the end 84 includes pairs of slit means as at 92 extend generally throughout the first section denoted by the numeral 94. The second section 96 adjacent end 86 includes similar slit means as at 98. A third section is spaced between the two sections and is generally denoted by the numeral 100. The slit means generally denoted by the numeral 98 in FIG. 3 are horizontal. However, as will be readily appreciated to those skilled in the art, when the alternative embodiment of male connection means 60 is used, vertical slit means 98' depicted in FIGS. 12 and 13 may be used and serve as the female connection member.

Figure 1:
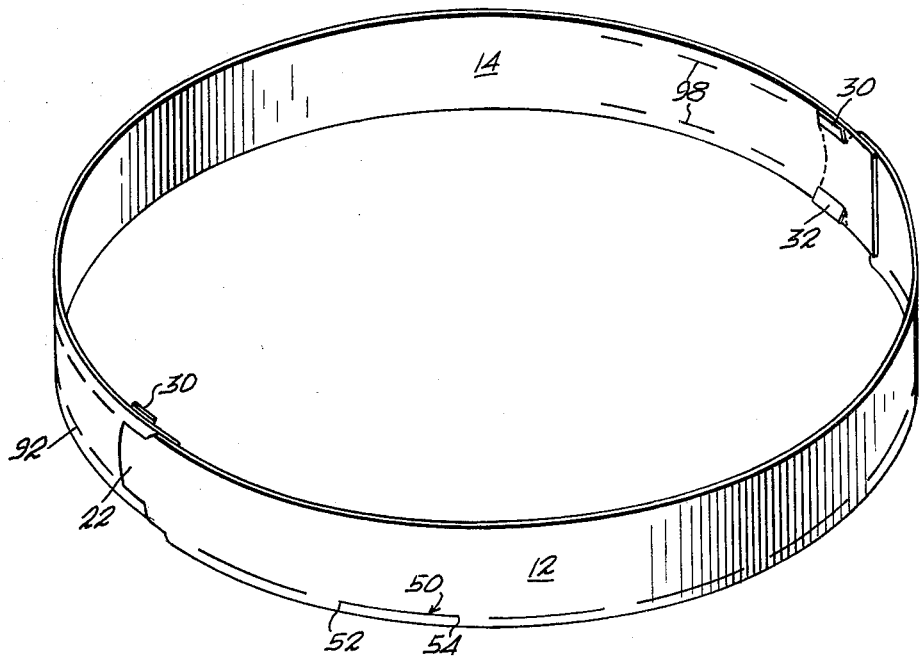
FIG. 1 is an elevational view of the first and second band members in hooked-up engagement.

Thereby, the two band members 12 and 14 may be connected as depicted in FIG. 1 with the male connection means 20 and 44 captivated by slit means 92 and 98 respectively. The various pairs of slit means enable the bands to be of an adjustable diameter dependant upon the number of pairs of slits and the spacing, the band comprising the first and second portions is doubly adjustable whether the embodiment shown in FIGS. 12 and 13 is used or the embodiment shown in FIGS. 2 and 3 is used.

Figure 10:
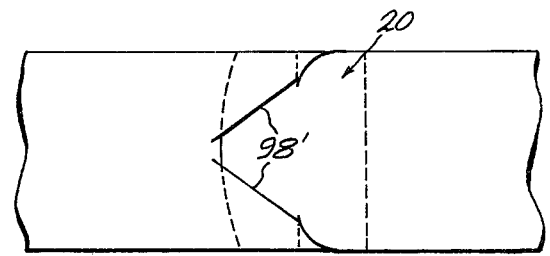
FIG. 10 is a partial fragmentary view of an alternative embodiment of first and second connection means in hooked-up connection.
Figure 11:
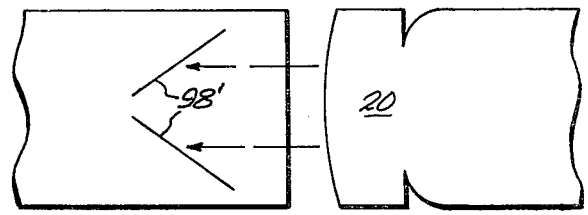
FIG. 11 is an elevational plan view of the alternative embodiment shown in FIG. 10.

Referring particularly to FIGS. 10 and 11 there is shown an alternative embodiment of the connection means wherein the male connection member 20 is connected to slit means 98' wherein each slit pair is angled at approximately 45° to one another forming a V-shaped slit means or female connection member. It has been found in practice that the embodiment shown in FIGS. 10 and 11 has an advantage over the embodiment shown in FIGS. 2 and 3 in that the band members remain flat upon one another regardless of when tension is applied to the band members. Thus, if one were to pull upon the individual band members 12 and 14 using the embodiment shown in FIG. 2 a ripple would appear in that the terminal edge of the first band member would ride above the second band member at the respective slit means forming a ripple or dimple, whereas if the alternative embodiment shown in FIGS. 10 and 11 were used, no such ripple or dimple effect would occur.

The alternative embodiment shown in FIGS. 12 and 13 offers the advantage of being an easily mountable male and female connection members since there is only one slit required in the second band member whereas in the embodiments shown in FIGS. 10 and 11 and FIGS. 2 and 3 there are pairs of slits required. Thus, the embodiment shown in FIGS. 12 and 13 would require one less production step during the manufacture of the second band member portion.

Figure 4:
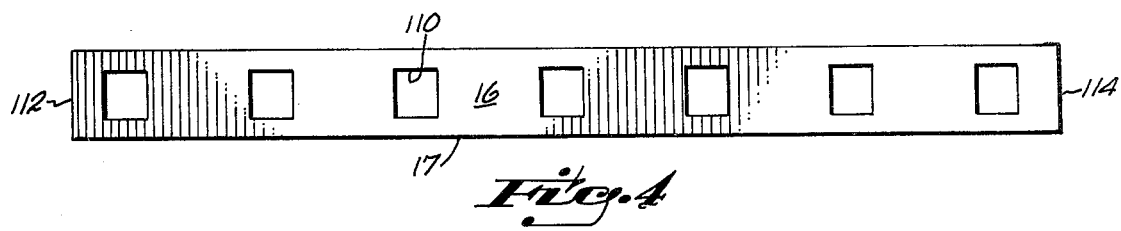
FIG. 4 is an elevational view of the reinforcing member.

A reinforcing member generally denoted by the numeral 16 in FIG. 4 is provided and serves among other things to keep the brim member and first band member generally flat against one another as will be described more fully hereinafter. The reinforcing member is generally equal to but slightly less than the front member 12 and is approximately equal to the distance between the male connection means heads 20 and 44 in the embodiment shown in FIGS. 2 and 3. A plurality of generally rectangular openings are provided in the reinforcing member 16 and generally denoted by the numeral 110. The openings are spaced apart from ends 112 throughout the band to end 114 a predetermined distance and are generally sized and shaped to mate compatibly with the brim male connection means as will be described more fully hereinafter.

Referring particularly to FIG. 6, there is shown the brim member 18 comprising a visor portion 116 having an inside abutment edge 118 and a plurality of male connection means spaced along the inside abutment edge 118 as at 120 which are sized and shaped for compatible locking interengagement with the spaced apart openings 110 of reinforcing member 16.

Each male connection means 120 includes a head portion 122 having side straight edges 124 and 126 with a generally arcuate terminal edge 128 and a neck portion 130 connecting the head portion 120 to the inside abutment edge 118.

IN USE

Figure 7:
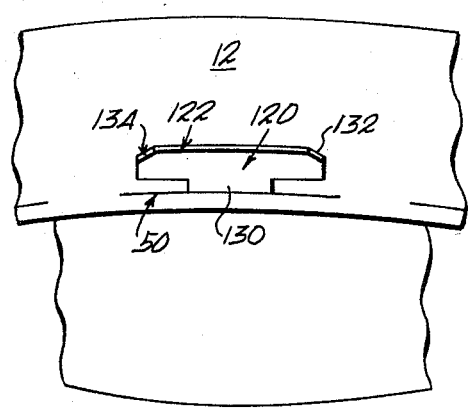
FIG. 7 is a sectional view of the brim member being inserted into the first band member.
Figure 8:
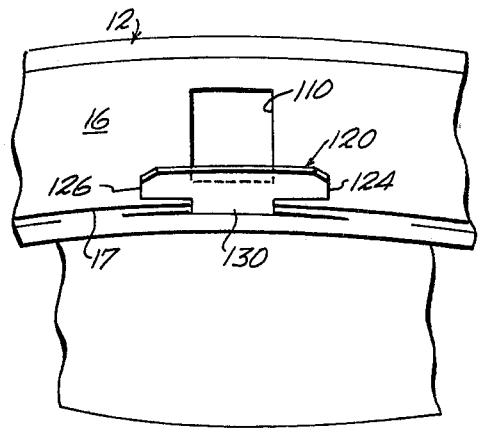
FIG. 8 is an elevational fragmentary view of the brim member being inserted into the band member with the reinforcing member laid over the first band member.

As can be seen in FIGS. 7 and 8, the brim member male connection means 120 is inserted through band member 12, slit means 50. It has been found in use that if the terminal edge of head member 122 are slightly truncated as at 132 and 134 the mounting and sliding of the head 120 through the slit 50 is somewhat more easily accomplished. The neck portion 130 then rests within the slit 50 as shown.

Referring particularly to FIG. 8, there can be seen the next step in the operation of assembling the kit. The reinforcing member 16 is applied to the first band member 12 with a lower edge 17 of the reinforcing member resting upon the neck portion 130 of the brim member and positioning the opening in line with its appropriate connection member 120.

Figure 9:
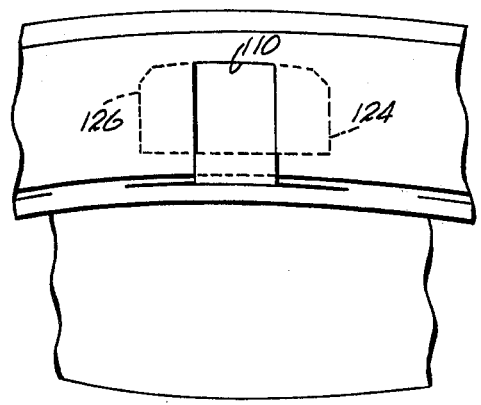
FIG. 9 is a partial fragmentary elevational view of the brim member, first band member and reinforcing member in hooked-up engagement.

As can be seen in FIG. 9, the side edges 126 and 124 of male connection means 120 are inserted into respective opening 110 for locking engagement of the brim member, reinforcing and first band member.

To finish assembling the hat, the first and second band members are connected as shown in FIG. 1 using whichever alternative embodiment most suits the user and the hat kit becomes a hat similar to the one shown in FIG. 5 and generally denoted by the numeral 10.

While the instant invention has been shown and described herein in what is conceived to be the most practical and preferred embodiment, it is recognized that departures may be made therefrom within the scope of the invention, which is therefore not to be limited to the details disclosed herein but is to be accorded the full scope of the claims so as to embrace any and all equivalent apparatus and articles.

What is claimed is:

1. An adjustable cap kit comprising:

a first band member of predetermined length defining a front band portion having a first end zone defining a first male connection means, a second end zone defining a second male connection means, upper and lower lateral edges spanning the first and second male connection means and spaced slit means along the first band member adjacent the lower edge, a second band member of a predetermined length defining a rear band portion having first and second ends, upper and lower edges spanning the ends, and slit means adjacent the upper and lower edges defining female connection means, sized and shaped for compatible locking engagement with the first and second male connection means, a reinforcing member having a predetermined length approximately equal to but slightly less than the length of the first member, the reinforcing member having equispaced openings therealong, the reinforcing member including first and second ends and upper and lower edges spanning the ends, and a brim member having a visor portion and an inside abutment edge with a plurality of male connection members spaced apart along the inside edge, the male connection members sized and shaped for locking connection with the first member slit means and the reinforcing member, each of said male connection members being spaced from one another and sized and configured for registry with and hooked-up engagement in the slit means of the first member and the openings of the reinforcing member, whereby the front and rear portions are adapted for locking engagement with one another through their respective male connection means and the female connection means, and the brim member is adapted for connection with the first band member and reinforcing member respectively.

2. An adjustable cap kit comprising:

a first band member of predetermined length defining a front band portion having a first end zone defining a first male connection means, a second end zone defining a second male connection means, upper and lower lateral edges spanning the first and second male connection means and spaced slit means along the first band member adjacent the lower edge, a second band member of a predetermined length defining a rear band portion having first and second ends, upper and lower edges spanning the ends, and slit means adjacent the upper and lower edges defining female connection means, sized and shaped for compatible locking engagement with the first and second male connection means, a reinforcing member having a predetermined length approximately equal to but slightly less than the length of the first member, the reinforcing member including first and second ends and upper and lower edges spanning the ends, and a brim member having a visor portion and an inside abutment edge with a plurality of male connection members spaced apart along the inside edge, the male connection members sized and shaped for locking connection with the first member slit means and the reinforcing member, each of said male connection members being spaced from one another and sized and configured for registry with and hooked-up engagement in the slit means of the front member and the openings of the reinforcing member, whereby the front and rear portions are adapted for locking engagement with one another through their respective male connection means and the female connection means, and the brim member is adapted for connection with the first band member and reinforcing member respectively.

3. An adjustable cap kit comprising:

a brim member, a first band member of predetermined length defining a front band portion having a first end zone defining a first male connection means, a second end zone defining a second male connection means, upper and lower lateral edges spanning the first and second male connection means and spaced slit means along the first band member adjacent the lower edge, a second band member of a predetermined length defining a rear band portion having first and second ends, upper and lower edges spanning the ends, and slit means adjacent the upper and lower edges defining female connection means, sized and shaped for compatible locking engagement with the first and second male connection means, an elongate reinforcing member having a predetermined length approximately equal to but slightly less than the length of the first member, the elongate reinforcing member including first and second ends and upper and lower edges spanning the ends, and said elongate reinforcing member comprising means to hold the brim member and the front band portion together;

a brim member having a visor portion and an inside abutment edge with a plurality of male connection members spaced apart along the inside edge, the male connection members sized and shaped for locking connection with the first member slit means and the reinforcing member, each of said male connection members being spaced from one another and sized and configured for registry with and hooked-up engagement in the slit means of the first member;

whereby the front and rear portions are adapted for locking engagement with one another through their respective male connection means and the female connection means, and the brim member is adapted for connection with the first band member and the elongate reinforcing member respectively.

4. The device as set forth in claim 1 or 3 wherein the front band portion includes a top lateral edge and wherein each male connection means comprises:

a head portion including a top tab having an upper straight edge generally horizontal and in the same plane as the front portion upper edge, a bottom tab having a lower straight edge generally horizontal but spaced a predetermined distance above the plane of the lower edge of the front band portion, a neck portion joining the head portion to the band portion comprising the band portion edges being inwardly arcuate in shape and defining upper and lower shoulder portions between the head and front band portions.

5. The device as set forth in claim 1 or 3 wherein the rear band portion comprises a first zone, a second zone and a third zone portion, the first and third zones having a plurality of slit means pairs comprising slits adjacent the upper and lower edges of the rear band portion, respectively and wherein each slit is spaced apart from its pair member a predetermined distance approximately equal to the distance between the top tab upper edge and the bottom tab lower edge.

6. The device as set forth in claim 1 wherein each spaced apart brim connection member comprises a head portion having an arcuate terminal end, side tabs, and a neck portion connecting the head portion and brim member.

7. The device as set forth in claim 5 wherein each slit along the rear band portion comprises angled slits, each slit being approximately 45° to the horizontal.

8. The device as set forth in claim 1 or 3 wherein the first and second portion, brim member and reinforcing member are made of a flexible plastic material.

9. The device as set forth in claim 1 or 3 wherein
the rear band portion is between 6 and 16 inches, the front band portion is between 6 and 12 inches, the reinforcing means is between $5\frac{1}{2}$ and 9 inches, and
the outside edge of the brim is of a radius of 16 inches, and
the inside edge of the brim is of a radius of approximately 8 inches.

* * * * *